(12) United States Patent
Black et al.

(10) Patent No.: US 6,505,758 B2
(45) Date of Patent: Jan. 14, 2003

(54) CARBONATED BEVERAGE DISPENSER

(75) Inventors: William J. Black, Gurnee, IL (US); Joseph Todd Piatnik, Bethel, CT (US); Amir Faroqui, Torrington, CT (US); Fernando Ubidia, Ludlow, MA (US)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 09/879,181

(22) Filed: Jun. 13, 2001

(65) Prior Publication Data

US 2002/0005413 A1 Jan. 17, 2002

Related U.S. Application Data

(60) Provisional application No. 60/211,211, filed on Jun. 13, 2000.

(51) Int. Cl.[7] .................................................. B67D 5/62
(52) U.S. Cl. .................................................. 222/146.6
(58) Field of Search ...................... 222/1, 129.1, 129.4, 222/146.6, 176, 396–399

(56) References Cited

U.S. PATENT DOCUMENTS

| | | | |
|---|---|---|---|
| 2,612,357 A | | 9/1952 | Parks |
| 3,224,641 A | * | 12/1965 | Morgan .................... 222/146.6 |
| 3,240,395 A | * | 3/1966 | Carver ..................... 222/146.6 |
| 3,721,369 A | | 3/1973 | Conti et al. |
| 4,148,334 A | | 4/1979 | Richards |
| 4,555,045 A | * | 11/1985 | Rodth et al. ............. 222/129.1 |
| 4,754,609 A | | 7/1988 | Black |
| 4,764,315 A | | 8/1988 | Brusa |
| 4,903,862 A | | 2/1990 | Shannon et al. |
| 4,960,228 A | * | 10/1990 | Takahashi et al. ....... 222/129.1 |
| 4,979,647 A | | 12/1990 | Hassell |
| 5,080,261 A | | 1/1992 | Green |
| 5,115,942 A | * | 5/1992 | Merrill et al. ................. 222/1 |
| 5,190,189 A | | 3/1993 | Zimmer et al. |
| 5,249,710 A | | 10/1993 | Hassell et al. |
| 5,251,790 A | * | 10/1993 | Cohn et al. .............. 222/146.6 |
| 5,310,088 A | | 5/1994 | Burrows |
| 5,319,947 A | | 6/1994 | Fischer |
| 5,350,086 A | | 9/1994 | Martin et al. |
| 5,353,958 A | | 10/1994 | Hawkins |
| 5,413,742 A | | 5/1995 | Gatter |
| 5,419,461 A | | 5/1995 | Goulet |
| 5,464,124 A | | 11/1995 | Weyh et al. |
| 5,487,492 A | | 1/1996 | Goulet |
| 5,549,219 A | * | 8/1996 | Lancaster ................. 222/129.1 |
| 5,765,726 A | | 6/1998 | Jones |

* cited by examiner

*Primary Examiner*—Philippe Derakshani
(74) *Attorney, Agent, or Firm*—Fitzpatrick, Cella, Harper & Scinto

(57) ABSTRACT

An apparatus for dispensing carbonated beverages includes a housing, an ice bin, a carbonator and a cold plate. The ice bin is disposed within the housing for storing ice and is surrounded by thermal insulation. The carbonator is disposed within the housing adjacent the ice bin and receives water and $CO_2$ gas to form carbonated water. The thermal insulation is disposed between the carbonator and the ice bin such that the ice bin is thermally isolated from the carbonator. The cold plate is chilled by the ice in the ice bin and includes pre-chilling coils for cooling the water to be supplied to the carbonator and post-chilling coils for cooling the carbonated water flowing from the carbonator.

21 Claims, 4 Drawing Sheets

CARBONATED BEVERAGE DISPENSER

This application claims the benefit of provisional Application No. 60/211,211, filed Jun. 13, 2000.

FIELD OF THE INVENTION

The present invention relates to beverage mixing and dispensing systems. More particularly, the present invention relates to beverage mixing and dispensing systems for effectively forming and dispensing carbonated water to be mixed in the beverages.

BACKGROUND OF THE INVENTION

Carbonated beverages or soft drinks are typically formed from a combination of syrup and carbonated water or soda. The carbonated water or soda is generated by entraining carbon dioxide ($CO_2$) gas into water under pressure in a carbonator. If an insufficient quantity of $CO_2$ gas is entrained in the water, the soda or resulting soft drink may have a "flat" taste, which is unacceptable to the consumer. Consistently providing a desired level of carbonation in soft drinks has been a problem in typical soft drink fountains.

It is known that the pressure of the $CO_2$ gas and the temperature of the water are parameters that affect the carbonation level of the carbonated water. As a rule of thumb, the colder the water, the greater the amount of $CO_2$ that can be entrained and maintained therein. However, the temperature of the supplied water to dispensing apparatuses varies from region to region and season to season. That is, in the United States, the temperature of public water in northern states is typically lower than that of public water supplied in southern states. Likewise, the temperature of water supplied in the winter is typically lower than that of water supplied in the summer in most regions. Thus, if the temperature of the water is unregulated, the carbonation levels will vary, possibly out of an acceptable range.

To avoid problems of varying temperature of supplied water, it has been known to chill the water supplied to the carbonator and, in some cases, to chill the carbonated water flowing from the carbonator. For example, U.S. Pat. No. 5,080,261 is directed to a soft drink dispenser that pre-chills water supplied to the carbonator and cools the carbonator itself. The dispenser includes an insulated ice bin for storing ice to be used in cups into which the soft drink is to be dispensed. The bottom plate of the ice bin is in thermal contact with a cooling plate made of high thermally conductive metal. An insulated, cylindrical carbonation and cooling tank includes a bottom plate that rests intimately upon the cooling plate. In addition, a baffle plate formed of thermally conductive material extends from the bottom plate into the carbonation tank to act as a cooling fin. The ice received within the ice bin acts as a heat sink for the cooling plate and the carbonation tank. The cooling plate includes a plurality of serpentine passages that are interconnected with a water supply conduit.

In use, supplied water is pre-chilled through the cooling plate and flows into the carbonation tank where pressurized $CO_2$ gas is supplied. The carbonated water in the carbonation tank is cooled due to the contact of the tank with the cooling plate and due to the cooling fin. When a dispensing valve is actuated to dispense a soft drink, carbonated water from the carbonation tank at a cold temperature can be mixed with a soft drink syrup and dispensed.

However, forming the carbonation tank in thermal contact with the cooling plate complicates the design of this dispensing apparatus, especially when forming the baffle plate of thermally conductive material to act as the cooling fin. Moreover, the ratio of the volume of water to the surface of the cold inner wall of the carbonator tank does not result in efficient cooling when compared with a cooling plate with serpentine passages.

U.S. Pat. No. 5,319,947 describes a beverage dispenser that includes a pre-chilled water cooling coil in a first cold plate for supplying chilled water to a carbonator, and a soda cooling coil in a second cold plate for cooling the carbonated water flowing from the carbonator. In addition, the second cold plate, which forms the bottom wall of an ice bin, is cast with an integral, semi-cylindrical sleeve extending therebelow to form a carbonator housing. The cylindrical carbonator is in intimate heat exchange contact with the sleeve in order to cool the carbonator by conduction.

However, such a casting with integral cold plate and carbonator sleeve is both difficult and expensive to manufacture.

SUMMARY OF THE INVENTION

It is, therefore, an aspect of the present invention to provide an apparatus for efficiently mixing and dispensing carbonated beverages.

It is another aspect of the present invention to provide an apparatus for efficiently forming carbonated beverages that is simple to manufacture and maintain.

In a first aspect of the present invention, an apparatus for dispensing carbonated beverages includes a housing, an ice bin, a carbonator and a cold plate. The housing has an exterior wall. The ice bin is disposed within the housing for storing ice and is surrounded by thermal insulation. The carbonator is disposed within the housing adjacent the ice bin and receives water and $CO_2$ gas to form carbonated water. The thermal insulation is disposed between the carbonator and the ice bin such that the ice bin is thermally isolated from the carbonator. The cold plate is chilled by the ice in the ice bin and includes pre-cooling coils for cooling the water to be supplied to the carbonator and post-cooling coils for cooling the carbonated water flowing from the carbonator.

In another aspect of the present invention, a method for forming carbonated beverages includes the steps of providing a pre-chilling unit and a post-chilling unit chilled by ice, and supplying water through the pre-chilling unit to an uncooled carbonator. The method further includes the steps of supplying pressurized $CO_2$ gas to the carbonator to mix with the chilled water and form carbonated water, and supplying the carbonated water to the post-chill unit to cool the carbonated water.

In still another aspect of the present invention, a carbonated beverage is formed by a method including the steps of providing a pre-chilling unit and a post-chilling unit chilled by ice, and supplying water through the pre-chilling unit to an uncooled carbonator. The method further includes the steps of supplying pressurized $CO_2$ gas to the carbonator to mix with the chilled water and form carbonated water, and supplying the carbonated water to the post-chill unit to cool the carbonated water.

The above, and other aspects, features and advantages of the present invention will be apparent from the following detailed description of the illustrated embodiments thereof which are to be read in connection with the accompanying drawings wherein:

DETAILED DESCRIPTION OF THE PREFERRED EMBODIMENTS

Figure 1:
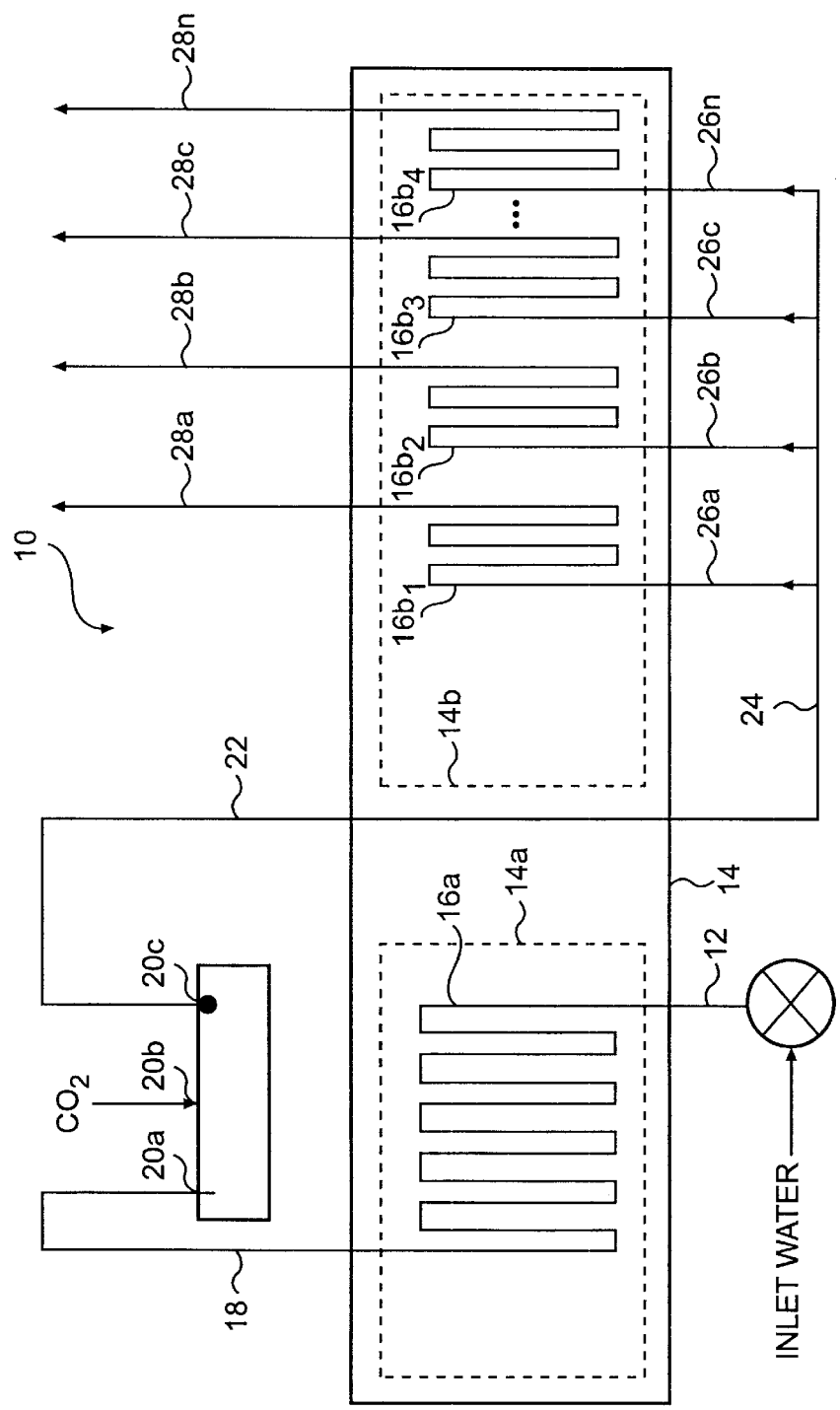
FIG. 1 is a schematic illustration of the components and the fluid flow of the dispensing apparatus of the present invention.

Referring to FIG. 1, the schematic description of the dispensing apparatus 10 of the present invention will be described. In order to form carbonated water or soda, water is mixed with pressurized $CO_2$ gas and the level of carbonation is dependent upon the temperature of the water and the pressure of the $CO_2$. The lower the water temperature, the more effectively the $CO_2$ is entrained and maintained in the water. It is therefore, an object of the present invention to chill the water to a suitable temperature prior to carbonation and to maintain the carbonated water at a chilled temperature until it is dispensed.

Referring to FIG. 1, water is supplied from a source through water inlet passage 12 to a cold plate 14. Cold plate 14 includes a pre-chill section 14a and a post-chill section 14b. Pre-chill section 14a includes serpentine cooling passages or coils 16a through which the inlet water flows. The chilled water exits cooling coils 16a through carbonator supply passage 18. Supply passage 18 is connected to carbonator 20 at inlet 20a, pressurized $CO_2$ gas is supplied to the carbonator at gas inlet 20b, and the resulting carbonated water exits the carbonator at outlet 20c into passage 22. The carbonated water is then supplied to post-chill section 14b of cold plate 14.

In a preferred embodiment, post-chill section 14b includes a series of cooling coils $16b_1$–$16b_n$. The number of post-chill coils is dependent upon the number of carbonated water heads to be used on the dispenser. For example, if carbonated water is to be dispensed from six heads, then six sets of post-chill coils are used. Alternatively, the carbonated water can be sent through one set of post-chill coils and then split downstream to the individual dispensing heads. If plural sets of post-chill coils are to be used, the carbonated water flows from passage 22 to a manifold 24 and then to the individual post-chill section inlets 26a–26n.

With the described arrangement, regardless of the temperature of the inlet water, the pre-chill coils ensure that the water entering carbonator 20 is at the desired temperature, approximately 35° F. The carbonated water is maintained at the desired temperature by sending the water through post-chill section 14b before being dispensed from the dispensing heads. Although it is desirable to chill the water throughout its flow before, during, and after carbonation, the present invention can avoid the cost and complexity of cooling the carbonator tank 20. Accordingly, with the present invention, the cooling source is thermally isolated from the carbonator tank as will become apparent from the description of FIG. 2.

Figure 2:
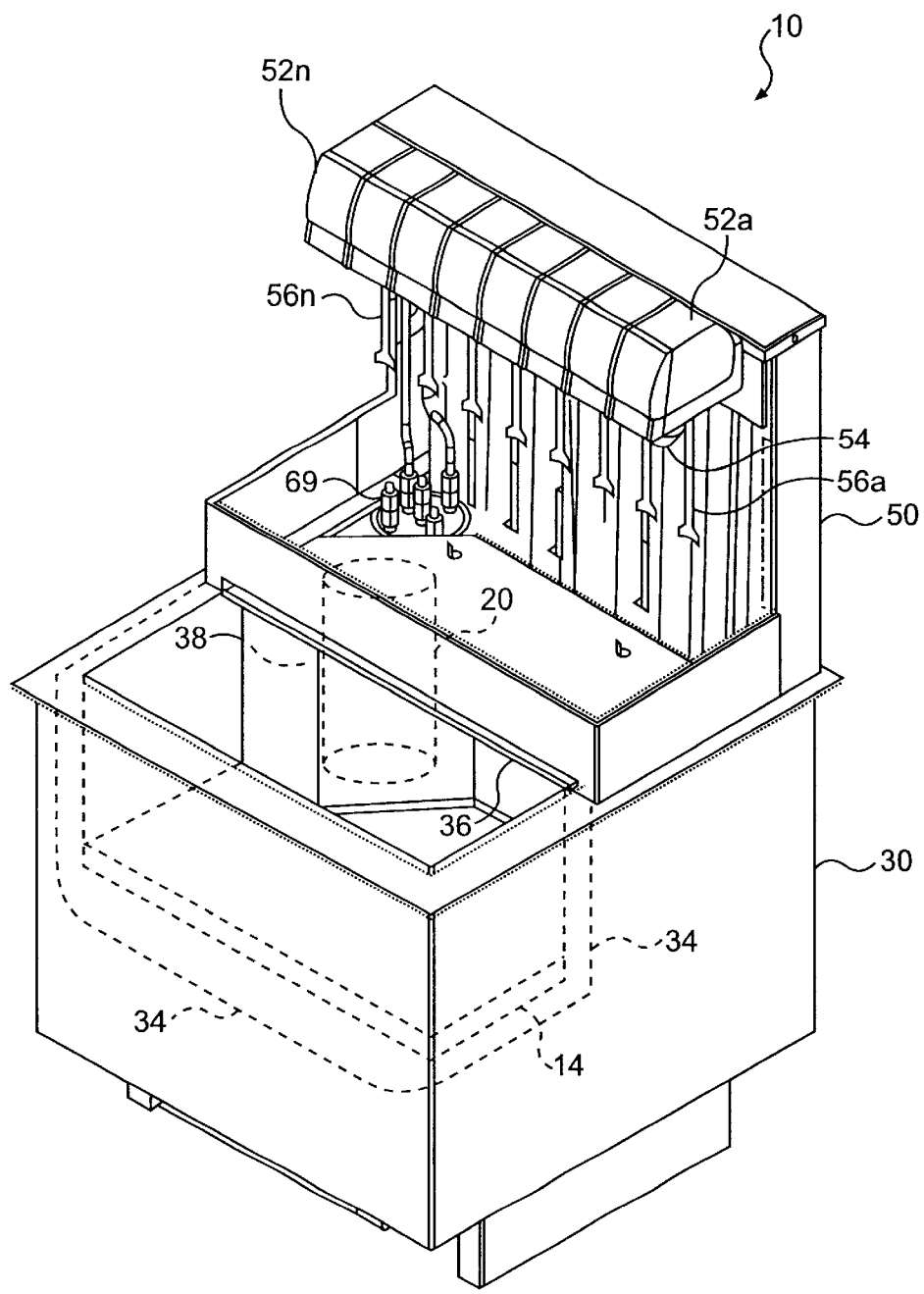
FIG. 2 is a perspective view of a dispensing apparatus of a first embodiment of the present invention.

In FIG. 2, a "drop-in" dispenser apparatus 10 will be described. This dispenser apparatus is self-contained and can be dropped into an aperture of a counter top. The apparatus includes two sections: a base section including housing 30, which is typically below the counter level, and a tower section 50. An ice bin 32 is disposed in housing 30. Ice, in cubed or crushed form, is placed in ice bin 32 for use in filling cups into which soft drinks are to be dispensed. The ice in bin 32 also acts as the cold source or heat sink of the carbonation system. Cold plate 14 forms the bottom of ice bin 32, or is in intimate thermal contact with the bottom of the ice bin.

In order to thermally insulate ice bin 32 and cold plate 14, a layer of insulation 34 is provided on the walls thereof. In addition, a displaceable lid 36 can cover the opening of ice bin 32 when not in use. Carbonator 20 is preferably housed within housing 30 in a space 38 between the insulation surrounding ice bin 32 and the walls of housing 30. As shown in FIG. 2, the water and gas connections of the carbonator protrude from a top plate of housing 30 for ease of connection.

Dispensing tower 50 of dispensing apparatus 10 includes plural dispensing heads 52a–52n. Each dispensing head includes a mixing nozzle 54 and a dispensing lever 56a–56n. If carbonated water is connected to a particular dispensing head, then depressing lever 56 will cause carbonated water to flow from dispensing head simultaneously with beverage syrup to be mixed in nozzle 54 and discharged into a cup.

Although carbonator 20 is not actively or passively cooled, it is nevertheless desirable to prevent heat gain in the carbonated water at the carbonator. This is achieved in at least two ways. First, carbonator space 38 is insulated from ambient environment by providing insulation on the interior surface of the walls forming housing 30. Second, the volume of the carbonator is decreased from that of a typical carbonator, so that the carbonated water will not sit long in the carbonator and gain heat.

A carbonator of a typical drop-in dispenser has a capacity of about 1.5 gallons. However, the carbonator of the present invention preferably has a capacity of about 55 ounces. Due to the relatively small capacity of carbonator 20, the water is cycled relatively quickly through the carbonator during use, thus providing less time for heat gain prior to flow through post-chill section 14b. Another advantage of the relatively small size of the carbonator is that it can fit compactly in a corner of housing 30 at the same level as ice bin 32, thus reducing the overall size of the dispensing apparatus.

Figure 3:
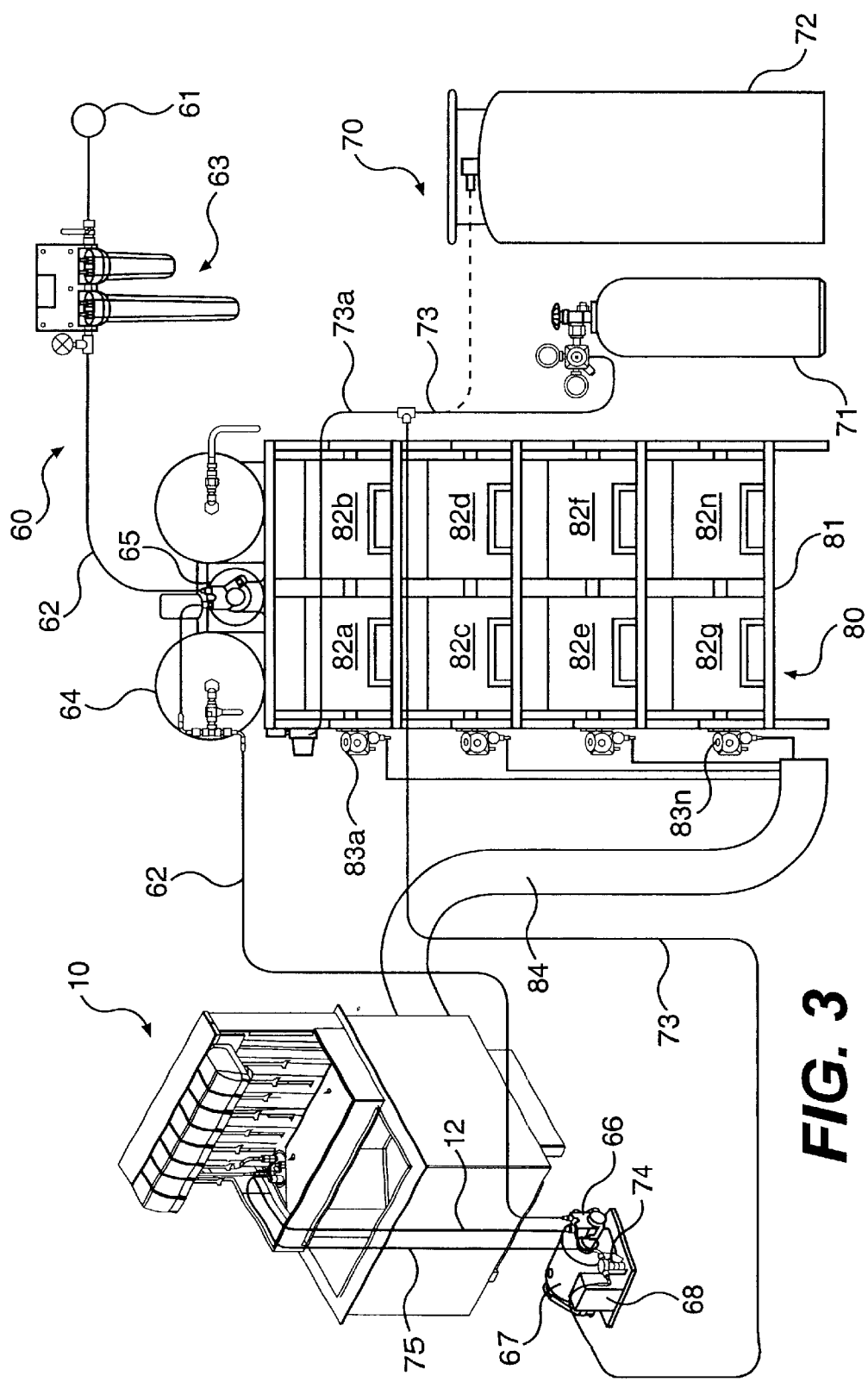
FIG. 3 is a perspective view of a dispensing system including the dispensing apparatus of the first embodiment.

How dispensing apparatus 10 is installed within the dispensing system will be described with reference to FIG. 3. The dispensing system includes the dispensing apparatus 10, a water supply section 60, a $CO_2$ supply section 70 and a soft drink syrup supply section 80. Water is supplied from a source 61, such as a municipal water main, to water supply line 62. Preferably, a series of filters, pressure regulators and a shut-off valve are incorporated into the water supply line as shown at 63. The flow of water to the dispensing apparatus 10 is preferably at a high rate of 125 gallons per minute. If the municipal supply cannot keep up with that demand, supplemental water can be stored in supplemental tanks 64 and controlled through regulator 65. The water is then supplied to high-flow water pump 66 driven by motor 67 to generate the high flow rate of 125 gallons per minute. The motor is driven by a controller 68 which receives an input from a carbonator volume sensor 69. When sensor 69 senses that the contents of the carbonator have reached the lower limit, controller 68 controls motor 67 to drive pump 66 and supply additional water to the carbonator.

The $CO_2$ supply section 70 includes a standard $CO_2$ tank 71 or a bulk $CO_2$ tank 72. Pressurized $CO_2$ flows through supply line 73 to a regulator 74 and to a carbonator connection line 75 into the carbonator.

Syrup supply section 80 includes a rack 81 upon which a plurality of syrup supply containers 82a–82n are stacked. Supply containers 82 can be of the well-known bag-in-box type. The syrups can include any of those provided by PepsiCo Inc. to form beverages known under any PepsiCo branded name, such as Pepsi-Cola®. Syrup is pumped from syrup supply containers 82 by syrup supply pumps 83a–83n. These pumps can be driven by $CO_2$ from tank 71 or 72 and supplied through a $CO_2$ gas branch line 73a. The outlet of the pumps is connected to a bundle of syrup supply passages 84 and connected to dispensing apparatus 10. If desired, the supplied syrup can be sent through discrete cooling coils of cooling plate 14 before being supplied to dispensing heads 52a–52n.

In the carbonator of a typical drop-in dispenser, the water is pumped in at a rate of about 100 gallons per hour and the $CO_2$ gas is supplied at a pressure of about 100 psi. However, due to the efficiency of carbonation of the present invention, the pressure of the $CO_2$ gas can be reduced to 75 psi and the water supply rate can be increased to 125 gallons per hour. Thus, not only can the usage of $CO_2$ be reduced, but also the throughput of the carbonator can be increased due to the higher water flow rate.

The operation of the dispensing system of the present invention will now be described. When the water supply system 60, $CO_2$ supply system 70 and syrup supply system 80 are appropriately connected to dispensing apparatus 10, and ice bin 32 is filled with ice, the system is ready for operation. Water pump 66 supplies water through supply line 12 through pre-chill section 14a of cooling plate 14 to carbonator 20. Concurrently, $CO_2$ gas is supplied through line 75 to the carbonator. Carbonated water is then formed in carbonator 20. When a carbonated beverage is desired, an operator places a cup under one of the dispensing heads 52 and depresses the desired lever 56. Carbonated water then flows from carbonator 20 through post-chill section 14b of cooling plate 14 and out the dispensing head. At the same time, the appropriate beverage syrup is pumped to the dispensing head and mixed with the carbonated water in mixing nozzle 54 and dispensed into the cup. As the carbonator exhausts its contents, it refills with chilled water and pressurized $CO_2$ gas. The mixed carbonated beverage is dispensed at the desired chilled temperature and at an appropriate carbonation level.

Figure 4:
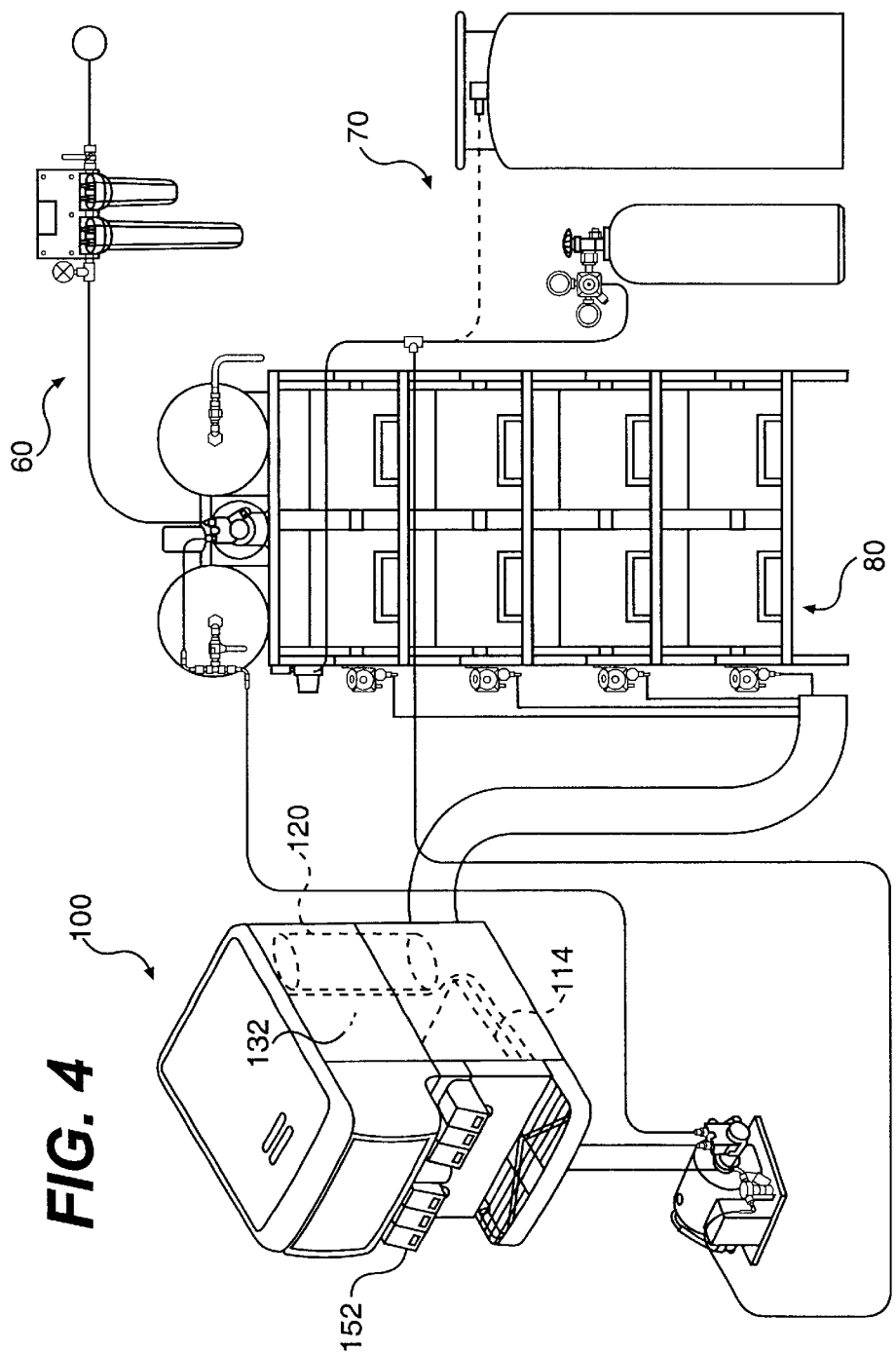
FIG. 4 is a perspective view of a dispensing system using a dispensing apparatus of a second embodiment of the present invention.

A dispensing system using a dispensing apparatus according to a second embodiment will be described with reference to FIG. 4. Components similar to those in the first embodiment are designated with the same reference numerals. The dispensing apparatus 100 of the second embodiment is of a counter top type. In dispensing apparatus 100, an insulated ice bin 132 is disposed behind the dispensing heads 152. Cold plate 114 is disposed below the bottom plate of ice bin 132. Carbonator 120 is disposed in space 138, which is insulated from ice bin 132. In the second embodiment, the connections between dispensing apparatus 100 and the water supply system 60, $CO_2$ supply system 70 and syrup supply section 80 are similar to that in the first embodiment. The carbonation and dispensing operation of the second embodiment is also similar to that of the first embodiment.

While the present invention has been described as to what is currently considered to be the preferred embodiments, it is to be understood that the invention is not limited to them. To the contrary, the invention is intended to cover various modifications and equivalent arrangements within the spirit and scope of the appended claims. The scope of the following claims is to be accorded the broadest interpretation so as to encompass all such modifications and equivalent structures and functions.

What is claimed is:

1. An apparatus for dispensing carbonated beverages, said apparatus comprising:

a housing having an exterior wall;

an ice bin disposed within said housing for storing ice, said ice bin being surrounded by thermal insulation;

a carbonator disposed within said housing adjacent said ice bin, said carbonator receiving water and $CO_2$ gas to form carbonated water, said thermal insulation disposed between said carbonator and said ice bin such that said ice bin is thermally isolated from said carbonator; and a cold plate chilled by the ice in said ice bin, said cold plate including pre-cooling coils for cooling the water to be supplied to said carbonator and post-cooling coils for cooling the carbonated water flowing from said carbonator.

2. An apparatus according to claim 1, wherein additional thermal insulation is disposed on interior surfaces of the exterior wall of said housing.

3. An apparatus according to claim 1, wherein said carbonator is disposed in a space between said ice bin and the exterior wall of said housing.

4. An apparatus according to claim 3, wherein said carbonator is disposed at a same height level as that of said ice bin.

5. An apparatus according to claim 1, wherein said carbonator comprises a low-volume tank.

6. An apparatus according to claim 5, wherein said low-volume tank has a capacity of about 55 ounces.

7. An apparatus according to claim 1, further comprising a high-flow water pump for supplying the water to said carbonator.

8. An apparatus according to claim 7, wherein said high-flow pump discharges water at a rate of about 125 gal/hr.

9. An apparatus according to claim 1, wherein the $CO_2$ gas is supplied to said carbonator at a pressure of about 75 psi.

10. A method for forming carbonated beverages, said method comprising the steps of:

providing a pre-chilling unit and a post-chilling unit chilled by ice;

supplying water through the pre-chilling unit to an uncooled carbonator;

supplying pressurized $CO_2$ gas to the carbonator to mix with the chilled water and form carbonated water; and supplying the carbonated water to the post-chilling unit to cool the carbonated water.

11. A method according to claim 10 wherein the carbonator comprises a low-volume tank.

12. A method according to claim 11, wherein the low-volume tank has a capacity of about 55 ounces.

13. A method according to claim 10, wherein the water is supplied to the carbonator at a rate of about 125 gallons per hour.

14. A method according to claim 10, wherein the $CO_2$ is supplied to the carbonator at a pressure of about 75 psi.

15. A carbonated product formed by a method comprising the steps of:

providing a pre-chilling unit and a post-chilling unit chilled by ice;

supplying water through the pre-chilling unit to an uncooled carbonator;

supplying pressurized $CO_2$ gas to the carbonator to mix with the chilled water and form carbonated water; and supplying the carbonated water to the post-chilling unit to cool the carbonated water.

16. A product according to claim 15, wherein the carbonator comprises a low-volume tank.

17. A product according to claim 16, wherein the low-volume tank has a capacity of about 55 ounces.

18. A product according to claim 15, wherein the water is supplied to the carbonator at a rate of about 125 gallons per hour.

19. A product according to claim 15, wherein the $CO_2$ is supplied to the carbonator at a pressure of about 75 psi.

20. A product according to claim 15, wherein the carbonated water is mixed with a syrup to form the carbonated product.

21. A product according to claim 20, wherein the syrup is for forming Pepsi-Cola®.

* * * * *